US007910338B2

(12) United States Patent
Hennessey et al.

(10) Patent No.: US 7,910,338 B2
(45) Date of Patent: *Mar. 22, 2011

(54) INTEGRATION OF ALTERNATIVE FEEDSTREAMS FOR BIOMASS TREATMENT AND UTILIZATION

(75) Inventors: Susan Marie Hennessey, Avondale, PA (US); Julie Friend, Claymont, DE (US); James B. Dunson, Jr., Newark, DE (US); Melvin P. Tucker, III, Lakewood, CO (US); Richard T. Elander, Evergreen, CO (US); Bonnie Hames, Westminster, CO (US)

(73) Assignees: E. I. du Pont de Nemours and Company, Wilmington, DE (US); Alliance for Sustainable Energy LLC, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/402,756

(22) Filed: Apr. 12, 2006

(65) Prior Publication Data

US 2007/0037259 A1 Feb. 15, 2007

Related U.S. Application Data

(60) Provisional application No. 60/670,437, filed on Apr. 12, 2005.

(51) Int. Cl.
  *C12P 7/00* (2006.01)
  *C12P 19/00* (2006.01)
  *C12P 19/14* (2006.01)
(52) U.S. Cl. ............. 435/99; 435/41; 435/72; 162/22; 426/7
(58) Field of Classification Search .......... 435/41, 435/72, 99; 426/7; 162/22
  See application file for complete search history.

(56) References Cited

U.S. PATENT DOCUMENTS

| 4,136,207 A | 1/1979 | Bender |
| 4,186,658 A | 2/1980 | Brown |
| 4,461,648 A | 7/1984 | Foody |
| 4,859,283 A | 8/1989 | Jayawant |
| 5,008,473 A | 4/1991 | Breitkopf et al. |
| 5,037,663 A | 8/1991 | Dale |
| 5,192,673 A | 3/1993 | Jain et al. |
| 5,231,017 A * | 7/1993 | Lantero et al. .............. 435/161 |
| 5,356,812 A | 10/1994 | Matsuyama et al. |
| 5,366,553 A | 11/1994 | Lair et al. |
| 5,705,369 A | 1/1998 | Torget et al. |
| 5,879,463 A | 3/1999 | Proenca |
| 5,916,780 A | 6/1999 | Foody et al. |
| 6,013,494 A | 1/2000 | Nakamura et al. |
| 6,090,595 A | 7/2000 | Foody et al. |
| 6,159,738 A | 12/2000 | Donnelly et al. |
| 6,228,630 B1 | 5/2001 | Kofod et al. |
| 6,254,914 B1 | 7/2001 | Singh et al. |
| 6,358,716 B1 | 3/2002 | Bulthuis et al. |
| 6,358,717 B1 | 3/2002 | Blaschek et al. |
| 6,514,733 B1 | 2/2003 | Emptage et al. |
| 6,777,207 B2 | 8/2004 | Kjeldsen et al. |
| 6,861,237 B2 | 3/2005 | Andersen et al. |
| 6,962,805 B2 | 11/2005 | Asakura et al. |
| 2003/0162271 A1 | 8/2003 | Zhang et al. |
| 2003/0170834 A1 | 9/2003 | Gatenby et al. |
| 2004/0016525 A1 | 1/2004 | Gervais |
| 2004/0231060 A1 | 11/2004 | Burdette et al. |
| 2005/0161038 A1 | 7/2005 | Pinatti et al. |
| 2005/0250192 A1 | 11/2005 | Shanmugam et al. |
| 2006/0003429 A1 | 1/2006 | Frost et al. |
| 2007/0031918 A1 | 2/2007 | Dunson et al. |

FOREIGN PATENT DOCUMENTS

| EP | 0263515 A2 | 4/1988 |
| EP | 0332234 B1 | 9/1989 |
| EP | 0 136 359 A1 | 4/1991 |
| FR | 656385 | 5/1929 |
| JP | 47004505 | 3/1972 |
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| JP | 62-3776 | 1/1987 |
| JP | 10035/81 | 1/1989 |
| JP | 1-93776 | 4/1989 |
| JP | 3-207079 | 9/1991 |
| JP | 3207079 | 9/1991 |
| JP | 4-50572 | 2/1992 |
| JP | 8-59681 | 3/1996 |
| JP | 3723579 | 9/2005 |

(Continued)

OTHER PUBLICATIONS

Shojaosadati et al. 1996. The Use of Biomass and Stillage Recycle in Conventional Ethanol Fermentation. J. Chem. Tech. Biotechnol. 67:362-366.*

(Continued)

*Primary Examiner* — Taeyoon Kim

(57) ABSTRACT

The present invention provides a method for treating biomass composed of integrated feedstocks to produce fermentable sugars. One aspect of the methods described herein includes a pretreatment step wherein biomass is integrated with an alternative feedstream and the resulting integrated feedstock, at relatively high concentrations, is treated with a low concentration of ammonia relative to the dry weight of biomass. In another aspect, a high solids concentration of pretreated biomass is integrated with an alternative feedstream for saccharifiaction.

37 Claims, No Drawings

FOREIGN PATENT DOCUMENTS

| | | |
|---|---|---|
| JP | 3899572 | 1/2007 |
| KR | 2001-0048482 * | 6/2001 |
| WO | WO 94/03646 | 2/1994 |
| WO | WO 03/078644 A2 | 9/2003 |
| WO | 2004/018645 A2 | 3/2004 |
| WO | 2007/041269 A2 | 4/2007 |
| WO | 2007/050671 A2 | 5/2007 |

OTHER PUBLICATIONS

L.R. Lynd et. al., Microbial Cellulose Utilization Fundamentals and Biotechnology, Microbiology and Molecular Biology Reviews, 2002, pp. 506-577, vol. 66.

Enzyme Nomenclature. Recommendation 1992, Supplement: Correction and Additions, Eur. J. Biochem., 1994, pp. 1-5, vol. 223.

Enzyme Nomenclature. Recommendation 1992, Supplement 2: Corrections and Additions, Eur. J. Biochem., 1995, pp. 1-6, vol. 232.

Enzyme Nomenclature. Recommendation 1992, Supplement 3: Corrections and Additions Eur. J. Biochem., 1996, pp. 1-5, vol. 237.

Enzyme Nomeclature. Recommendation 1992, Supplement 4: Corrections and Additions, Eur. J. Biochem., 1997, pp. 1-6, vol. 250.

Enzyme Nomenclature. Recommendation 1992, Supplement 5, Eur. J. Biochem., 1999, pp. 610-650, vol. 264.

G.L. Miller, Use of Dinitrosalicylic Acid Reagent for Determination of Reducing Sugar, Anal. Chem., 1959, pp. 426-428, vol. 31.

Jones et. al., Acetone-Butanol Fermentation Revisted, Microbiol. Rev., 1986, pp. 484-524, vol. 50.

Underwood et. al., Genetic Changes to Optimize Carbon Partitioning Between Ethanol and Biosynthesis in Ethanologenic *Escherichia coli*, App. Environ. Microbiol., 2002, pp. 6263-6272, vol. 68.

Zhou et. al., Production of Optically Pure D-Lactic Acid in Mineral Salts Medium by Metabolically Engineered *Escherichia coli* W3110, Appl. Environ. Microbiol., 2003, pp. 399-407, vol. 69.

Tay et. al., Production of L(+) Lactic Acid From Glucose and Starch by Immobilized Cells of *Rhizopus oryzae* in a Rotating Fibrous Bed Bioreactor, Biotechnol. Bioeng., 2002, pp. 1-12, vol. 80.

Niu et. al., Benzene-Free Synthesis of Adipic Acid, Biotechnol. Prog., 2002, pp. 201-211, vol. 18.

Cheryan et. al., Production of Acetic Acid by *Clostridium thermoaceticum*, Adv. Appl. Microbiol., 1997, pp. 1-33, vol. 43.

Freer, Acetic Acid Production by Dekkera/Brettanomyces Yeasts, World J. Microbiol. Biotechnol., 2002, pp. 271-275, vol. 18.

Lin et. al., Metabolic Engineering of Aerobic Succinate Production Systems in *Escherichia coli* to Improve Process Productivity and Achieve the Maximum Theoretical Succinate Yield, Metab. Eng., 2005, pp. 116-127, vol. 7.

Li et. al., Efficient Pyruvate Production by a Multi-Vitamin Auxotroph of *Torulopis glabrata*: Key Role and Optimization of Vitamin Levels, Appl. Microbiol. Biotechnol., 2001, pp. 680-685, vol. 55.

Yokota et. al., Pyruvic Acid Production by an F-ATPASE-Defective Mutant of *Escherichia coli* W1485LIP2, Biosci. Biotech. Biochem., 1994, pp. 2164-2167, vol. 58.

Suwannakham et. al., Enhanced Propionic Acid Fermentation by Propionibacterium Acidpropionic Mutant Obtained by Adaptation in a Fibrous-Bed Bioreactor, 2005, pp. 325-337, vol. 91.

Wu et. al., Extractive Fermentation for Butyric Acid Production From Glucose by *Clostridium tyrobutyricum*, Biotechnol. Bioeng., 2003, pp. 93-102, vol. 82.

Janssen, Propanel As an End Product of Theronine Fermentation, Arch. Microbiol., 2004, pp. 482-486, vol. 182.

Anantassiadis et. al., Process Optimization of Continuous Gluconic Acid Fermentation by Isolated Yeast-Like Strains of *Aureobasidium pullulans*, Biotechnol. Bioeng., 2005, pp. 494-501, vol. 91.

Singh et. al., Optimisation of Fermentation Conditions for Gluconic Acid Production by a Mutant of *Aspergillus niger*, Indian J. Exp. Biol., 2001, pp. 1136-1143, vol. 39.

Elfari et. al., A Gluconobacter Oxydans Mutant Converting Glucose Almost Quantitatively to 5-Keto-D-Gluconic Acid, Appl. Microbiol. Biotechnol., 2005, pp. 668-674, vol. 66.

Reddy et. al., Enhanced Production of Itaconic Acid From Corn Starch and Market Refuse Fruits by Genetically Manipulated *Aspergillus terreus* SKR10, Bioresour. Technol., 2002, pp. 69-71, vol. 85.

Ikram-Ui-Haq et. al., Optimization of Nitrogen for Enhanced Citric Acid Productivity by a 2-Deoxy D-Glucose Resistant Culture of *Aspergillus niger* NGD-280, Bioresour. Technol., 2005, pp. 645-648, vol. 96.

Mussatto et. al., Xylitol Production Form High Xylose Concentration: Evaluation of the Fermentation in Bioreactor Under Different Stirring Rates, J. Appl. Microbiol., 2003, pp. 331-337, vol. 95.

Gorenflo et. al., Development of a Process for the Biotechnological Large-Scale Production of 4-Hydroxyvalerate-Containing Polyesters and Characterization of Their Physical and Mechanical Properties, Biomacromolecules, 2001, pp. 45-57, vol. 2.

Ui et. al., Production of L-2,3-Butanediol by a New Pathway Constructed in *Escherichia coli*, Lett. Appl. Microbiol., 2004, pp. 533-537, vol. 39.

Nakayama et. al., Fermentative Production of L-Arginine, Arg. Biol. Chem., 1972, pp. 1675-1684, vol. 36.

Okamoto et. al., Development of an Industrially Stable Process for L-Threonine Fermentation by an L-Methionine-Auxotrophic Mutant of *Escherichia coli*, J. Biosci. Bioeng., 2000, pp. 87-89, vol. 89.

Kumar et. al., Effect of Cysteine on Methionine Production by a Regulatory Mutant of *Corynebacterium lilium*, Bioresour. Technol., 2005, pp. 287-294, vol. 96.

Durre, New Insights and Novel Developments in Clostridial Acetone/ Butanol/Isopropanol Fermentation, Appl. Microbiol. Biotechnol., 1998, pp. 639-648, vol. 49.

Groot et. al., Technologies for Butanol Recovery Intergrated With Fermentations, Process Biochem., 1992, pp. 61-75, vol. 27.

Barron et al>, "Ethanol production by *Kluyveromyces marxianus* IMB3 during growth on straw-supplemented whiskey distillery spent wash at 45 degrees C"., Bioprocess Engineering, vol. 17, No. 6, Nov. 1997, pp. 383-386.

Kurakake et al., "Pretreatment with Ammonia Water for Enzymatic Hydrolysis of Corn Husk, Bagasse, and Switchgrass", Applied Biochemistry and Biotechnology, vol. 90, No. 3, Mar. 2001, pp. 251-259.

Ben-Ghedalia et al., "The Effect of Chemical Pretreatments and Subsequent Enzymatic Treatments on the Organic Matter Digestibility in Vitro of Wheat Straw", Nutrition Reports International, vol. 19, No. 4, Apr. 1979, pp. 499-505.

Waiss et al., "Improving Digestibility of Straws for Ruminant Feed by Aqueous Ammonia", Journal of Animal Science, vol. 35, No. 1, 1972, pp. 109-112.

Joblin et al., "Fermentation of barley straw by anaerobic rumen bacteria and fungi in axenic culture and in co-culture with methanogens", Letters in Applied Microbiology, vol. 9, No. 5, 1989, pp. 195-197.

Taylor et al., "Corn-Milling Pretreatment with Anhydrous Ammonia", Applied Biochemistry and Biotechnology, vol. 104, No. 2, Feb. 2003, pp. 141-148.

Cao et al., "Ethanol production from corn cob pretreated by the ammonia steeping process using genetically engineered yeast", Biotechnology Letters, vol. 18, No. 9, 1996, pp. 1013-1018.

Iyer et al., "Ammonia Recycled Percolation Process for Pretreatment of Herbaceous Biomess", Applied Biochemistry and Biotechnology, vol. 57/58, 1996, pp. 121-132.

Mosier et al., "Features of promising technologies for pretreatment of lignocellulosic biomass" Bioresource Technology, vol. 96, No. 6, Apr. 2005, pp. 673-686.

PCT International Search Report and Written Opinion for International Application No. PCT/US2006/014144 dated Oct. 17, 2006.

U.S. Appl. No. 11/403,087, filed Apr. 12, 2006, James B. Dunson et al.

U.S. Appl. No. 11/402,757, filed Apr. 12, 2006, James B. Dunson et al.

U.S. Appl. No. 11/741,892, filed Apr. 30, 2007, Gail K. Donaldson et al.

U.S. Appl. No. 11/741,916, filed Apr. 30, 2007, Gail K. Donaldson et al.

U.S. Appl. No. 60/847,813, filed Sep. 28, 2006, Paul V. Viitanen et al.

U.S. Appl. No. 60/847,856, filed Sep. 28, 2006, Paul V. Viitanen et al.

U.S. Appl. No. 11/402,464, filed Apr. 12, 2006, James B. Dunson et al.

Gould, Alkaline Peroxide Delignification of Agricultural Residues to Enhance Enzymatic Saccharification, Biotech and Bioengr., 1984, vol. 26:46-52.

L. Teixeira et. al., Alkaline and Peracetic Acid Pretreatments of Biomass for Ethanol Production, Appl. Biochem. and Biotech., 1999, 77-79:19-34.

A. Elshafei et. al., The Saccharification of Corn Stover by Cellulase From *Penicillium funiculosum*, Bioresource Tech., 1991, vol. 35:73-80.

T. Kim et. al., Pretreatment and Fractionation of Corn Stover by Ammonia Recycle Percolation Process, Bioresource Technology, 2005, vol. 96:2007-2013.

Ryu et al., Bioconversion of Waste Cellulose by Using an Attrition Bioreactor, Biotechnol. Bioeng., 1983, vol. 25:53-65.

Curreli et al., Complete and Efficient Enzymic Hydrolysis of Pretreated Wheat Straw, Process Biochem., 2002, vol. 37:937-941.

Teymouri et al., Optimization of the Ammonia Fiber Expolsion (AFEX) Treatment Parameters for Enzymatic Hydrolysis of Corn Stover, Bioresource Tech., 2005, vol. 96:2014-2018.

Cao et. al., Production of 2, 3 Butanediol From Pretreated Corn Cob by *Klebsiella oxytoco* in the Presence of Fungal Cellulase, Applied Biochemistryand Biotechnology, 1997, vol. 63-65:129-139.

H. Hagino, Control Mechanisma in Aromatic Amino Acid Biosynthesis and the Amino Acid Production, Arg. Chem. Soc., Japan, 1976, Vol. 50:R79-R87.

Aden et al., Biofuels for Sustainable Transportation, National Renewable Energy Laboratory Report TP-510-32438, 2000.

Lloyd et al., Appl. Application of a Depolymerization Model for Predicting Thermochemical Hydrolysis of Hemicellulose, Appl. Biochem. & Biotechnol., 2003, vol. 105:53-67.

Lloyd et al., Combined Sugar Yields for Dilute Sulfuric Acid Pretreatment of Corn Stover Followed by Enzymatic Hydrolysis of the Remaining Solids, Bioresource Technol., 2005, vol. 96:1967-1977.

Gusakov et al., Kinetics of the Enzymatic Hydrolysis of Cellulose: 1. Mathematical Model for a Batch Reactor Process, Enz. Microb. Technol., 1985, vol. 7:346-352.

Lee et al., Cellulose Hydrolysis Under Extremely Low Sulfuric Acid and High-Temperature Conditions, Appl. Biochem. Biotech., 2001, vol. 91:331-340.

Gusakov et al., Enhancement of Enzymatic Cellulose Hydrolysis Using a Novel Type of Bioreactor With Intensive Stirring Induced by Electromagnetic Field, Appl. Biochem. & Biotechnol., 1996, vol. 58:141-153.

Kim et al., Pretreatment of Corn Stover by Soakingin Aqueous Ammonia, Applied and Biochemistry and Biotechnology, 2005, vol. 121:1119-1131.

Teymouri, Farzaneh et al., Optimization of the ammonia fiber explosion (AFEX) treatment parameters for enzymatic hydrolysis of corn stover, Bioresource Technology, 2005, pp. 2014-2018, vol. 96, Elsevier Ltd.

Kim, Tae Hyun et al., Fractionation of corn stover by hot-water and aqueous ammonia treatment, Bioresource Technology, 2006, pp. 224-232, vol. 97, Elsevier Ltd.

Yoon, H. H. et al., Ammonia-Recycled Percolation Process for Pretreatment of Biomass Feedstock, Applied Biochemistry and Biotechnology, 1995, pp. 5-19, vol. 51/52, Humana Press, Inc.

Guggolz et al., J. Anim. Sci. 33:167-70 (1971), Enzymatic evaluation of processes for improving agricultural wastes for ruminant feeds.

Kim & Lee, Bioresour. Technol. 97:224-32 (2006), Fractionation of corn stover by hot-water and aqueous ammonia treatment.

Bush pushes fix for oil 'addiction', http://www.cnn.com/2006/POLITICS/01/31/sotu.energy/index, (2006) p. 1-3.

Fermentation of Lignocellulosic Biomass, http://www.wisbiorefine.org/proc/fermlig.pdf, (2007) p. 1-7.

Sugar from cellulosic biomass, http://www.americanenergyindependence.com/sugar.html, (2008) p. 1-12.

\* cited by examiner

INTEGRATION OF ALTERNATIVE FEEDSTREAMS FOR BIOMASS TREATMENT AND UTILIZATION

This application claims the benefit of U.S. Provisional Application No. 60/670,437, filed Apr. 12, 2005.

STATEMENT OF GOVERNMENT RIGHTS

This invention was made with United States government support under Contract No. 04-03-CA-70224 awarded by the Department of Energy. The government has certain rights in this invention.

FIELD OF THE INVENTION

The invention relates to the general field of biomass processing. Specifically, methods are provided for integrating alternative feedstreams including low-value co-products and waste streams from industrial processing, such as grain and other seed processing, into biomass for treatment and utilization in processes to produce high-value products.

BACKGROUND OF THE INVENTION

Cellulosic and lignocellulosic feedstocks and wastes, such as agricultural residues, wood, forestry wastes, sludge from paper manufacture, and municipal and industrial solid wastes, provide potentially large renewable feedstocks for the production of chemicals, plastics, fuels and feeds. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily available to saccharification enzymes for such hydrolysis. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose.

Current practices for utilizing biomass are generally directed to providing a stream of biomass, often times from one source, and pretreating the stream of biomass by the standard methods described above. Such practices do not take advantage of integrating multiple biomass streams, such as in-process streams or waste streams, at different steps of processing and do not include economically robust treatment processes for said integrated biomass streams.

In order to achieve an economically robust process that incorporates use of integrated biomass feedstreams, a commercial process that includes hydrolysis of carbohydrates in lignocellulose from integrated biomass feedstreams is needed. To achieve the economic viability, that process must also provide high yields of sugars at high concentrations, using low amounts of chemicals, and produce a source of fermentable sugars with low toxicity toward fermentative organisms that convert sugars to value-added chemicals and fuels.

The methods described herein address ways to incorporate said integrated feedstreams into economically robust processes that meet the above needed criteria for the production of value-added chemicals and fuels.

SUMMARY OF THE INVENTION

The present invention provides a method for treating biomass composed of integrated feedstocks to produce fermentable sugars.

One aspect of the methods described herein includes a pretreatment step wherein biomass is integrated with an alternative feedstream and the resulting integrated feedstock, at relatively high concentrations, is treated with a low concentration of ammonia relative to the dry weight of biomass. In another aspect, a high solids concentration of pretreated biomass is integrated with an alternative feedstream for saccharifiaction.

In one embodiment biomass is treated in a method comprising:
 a) providing biomass;
 b) adding to the biomass of a) at least one alternative feedstream to produce an integrated feedstock;
 c) contacting the integrated feedstock of b) with an aqueous solution comprising ammonia to form an integrated feedstock-aqueous ammonia mixture, wherein the ammonia is present at a concentration at least sufficient to maintain alkaline pH of the integrated feedstock-aqueous ammonia mixture but wherein said ammonia is present at less than about 12 weight percent relative to dry weight of integrated feedstock, and further wherein the dry weight of integrated feedstock is at high solids concentration of at least about 15 weight percent relative to the weight of the integrated feedstock-aqueous ammonia mixture, to produce a pretreated integrated feedstock product; and
 d) contacting the product of c) with a saccharification enzyme consortium under suitable conditions,
 to produce a fermentable sugar product.

In another embodiment, integrated feedstocks are treated and saccharified in a method comprising:
 a) providing biomass;
 b) subjecting the biomass of a) to a pretreatment process to produce a pretreated biomass product;
 c) adding to the pretreated biomass product of b) at least one alternative feedstream to produce a first or second integrated feedstock; and
 d) contacting the first or second integrated feedstock of c) with a saccharification enzyme consortium under suitable conditions,
 to produce a fermentable sugar product. In an aspect of this method, the pretreatment process in b) includes contacting the biomass with an aqueous solution comprising ammonia to form a biomass-aqueous ammonia mixture, wherein the ammonia is present at a concentration at least sufficient to maintain alkaline pH of the biomass-aqueous ammonia mixture but wherein said ammonia is present at less than about 12 weight percent relative to dry weight of biomass, and further wherein the dry weight of biomass is at a high solids concentration of at least about 15 weight percent relative to the weight of the biomass-aqueous ammonia mixture. In a further aspect of this method, the alternative feedstream that is added to the pretreated biomass product of b) comprises stillage produced during seed processing. In yet another aspect, the biomass of a) may or may not be an integrated feedstock as described herein.

The fermentable sugars resulting from the methods described herein, can then be used for the production of value-added chemicals, fuels or other high-value products.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides methods for treating biomass and alternative feedstreams, collectively referred to as "integrated feedstocks" to produce fermentable sugars. The fermentable sugars can then be used for the production of value added chemicals, fuels or other high-value products.

The alternative feedstreams include at least one low-value co-product, a processing stream and/or industrial processing waste stream.

Biomass and alternate feedstreams may be combined to form an integrated feedstock for pretreatment processing to achieve concurrent pretreatment of biomass and the co-product or process stream. Alternatively a non-integrated biomass may be pretreated, then the co-product or process stream added to the pretreated biomass forming a second integrated feedstock for saccharification. In both cases a pretreatment step is included wherein non-integrated biomass or integrated feedstock at relatively high concentration is treated with a relatively low concentration of ammonia relative to the dry weight of the initial material, and the ammonia-treated product is then digested with a saccharification enzyme consortium to produce fermentable sugars. The fermentable sugars are converted by biocatalysts to high value target products such as chemicals, plastics, and fuels.

Definitions:

In this disclosure, a number of terms are used. The following definitions are provided:

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T412 om-02 (Moisture in Pulp, Paper and Paperboard).

The term "target chemical" refers to a chemical produced by fermentation. Chemical is used in a broad sense and includes molecules such as proteins, including, for example, peptides, enzymes and antibodies.

A target chemical that is "derivable from biomass" is a target chemical produced by a process whereby biomass is hydrolyzed to release fermentable sugars, and the fermentable sugars are fermented using at least one biocatalyst to produce a desired target chemical.

The terms "plasticizer" and "softening agent" refer to materials that cause a reduction in the cohesive intermolecular forces along or between polymer chains. Such materials may act, for example, to decrease crystallinity, or disrupt bonds between lignin and non-lignin carbohydrate fibers (e.g., cellulose or hemicellulose).

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood, and forestry waste. Examples of biomass include, but are not limited to, corn grain, corn cobs, crop residues such as corn husks, corn stover, grasses, wheat, wheat straw, hay, barley, barley straw, rice straw, switchgrass, waste paper, sugar cane bagasse, sorghum, soy, trees, branches, roots, leaves, wood chips, sawdust, shrubs and bushes, vegetables, fruits, flowers and animal manure. In one embodiment, biomass that is useful for the invention includes biomass that has a relatively high carbohydrate value, is relatively dense, and/or is relatively easy to collect, transport, store and/or handle. In one embodiment of the invention, biomass that is useful includes corn cobs, corn stover and sugar cane bagasse.

"Alternative feedstream" or "alternative feedstock" includes a variety of materials that could benefit the overall process of converting biomass to fermentable sugars for the production of value added chemicals and/or fuels. Such feedstreams may be produced by industrial processing, including grain or seed processing, food processing, paper/pulp processing, etc. One type of such material includes co-products and wastes of grain or other seed processing, including corn dry grind processing, corn dry milling, and corn wet milling. As described herein, in some embodiments agricultural waste and/or industrial processing provide fibrous material that can be incorporated into pretreatment processing. In other embodiments industrial processing streams or other feedstreams (such as low-value or wastes streams) can be incorporated into biomass post-pretreatment to benefit further biomass processing steps including saccharification and fermentation. Non-limiting sources of low-value and wastes streams that may make-up an alternative feedstream include agricultural residues, such as corn or other crop hulls, municipal solid waste, industrial solid waste, sludge from paper manufacture, yard waste, wood and forestry waste.

"Integrated feedstocks" or "integrated feedstreams" means a combination of biomass and at least one alternative feedstream or feedstock.

For the purposes of this invention, an "aqueous solution comprising ammonia" refers to the use of ammonia gas ($NH_3$), compounds comprising ammonium ions ($NH_4^+$) such as ammonium hydroxide or ammonium sulfate, compounds that release ammonia upon degradation such as urea, and combinations thereof in an aqueous medium.

Integrated Feedstock for Pretreatment

An aspect of the present method includes combining any biomass feedstock with at least one alternative feedstream that is comprised of a low-value co-product or industrial processing stream, such as a waste stream.

As described above, industrial processing for the production of high value products, such as, oil, starch, protein, sugar syrup and ethanol, often produces low-value co-products, in-process streams and waste streams. In the present methods, these co-products are captured for recycling back into high value product processing streams or utilized to benefit processing for value added chemical and fuel production.

In one aspect of the claimed method, grain or other seed processing co-product or process stream that includes fiber may be combined with other biomass to provide an integrated feedstock that is pretreated.

The materials of interest comprising the alternative feedstock include low-value co-products, in-process streams and waste streams; which together are referred to as alternative streams. For example, a low-value co-product is one that is sold for animal feed. Examples of low starch or high oil seed process streams include hull streams that are separated in the processing of soybeans, sunflower seeds, peanuts and cottonseeds. Waste streams that contain fibrous material may also be used in preparing an integrated feedstock for pretreatment. Integrated feedstocks for pretreatment may include material containing fiber produced in the processing of any seed, for example, corn, oat, wheat, barley, rice, canola, sunflower, cotton, pea, soybean, and other legumes.

Soybeans are typically processed in the United States by solvent-extraction with hexane to recover the oil. Beans are cleaned and may be dried and allowed to equilibrate at 10-11% moisture to facilitate loosening of the seed coat or hull. They are then cracked, dehulled by screening and aspiration, and conditioned by treatment with steam (qv) to facilitate flaking. The conditioned meats are flaked and extracted with hexane to remove the oil. Hexane and the oil in the miscella are separated by evaporation and the hexane is recovered. (Kirk-Othmer Encyclopedia of Chemical Technology, 4th edition 1997). The seed coats or hulls removed during such processing may be used as an integrated feedstream in the present method.

Processing of sunflowers consists of screw-pressing, direct extraction with hexane, or prepress-solvent extraction. The latter is most commonly used in the United States. The first step is cleaning, followed by dehulling. The dehulled seed is conditioned by heating and then goes to screw presses or is flaked as in the case of direct solvent extraction with hexane. The screw-pressed cake is ground for use in feeds or granulated and extracted by hexane to recover the remaining oil. (Kirk-Othmer Encyclopedia of Chemical Technology, 4th edition 1997). The hulls removed during such processing may be used as an integrated feedstream in the present method.

Processing of peanuts for peanut oil is carried out by screw-pressing or prepressing, followed by solvent extraction. In screw-pressing, the peanuts are shelled, cooked, and pressed to yield a crude oil plus a cake containing ca 5% residual oil. The cake is ground, and the ground peanut hulls are blended back to adjust protein content. In prepressing-solvent extraction, the cooked meats are screw-pressed at low pressure to remove a portion of the oil and then extracted with hexane to reduce the residual oil to ca 1%. Residual hexane in the meal is recovered by applying jacket or live steam in a desolventizer. Hexane in the miscella is recovered by evaporation. (Kirk-Othmer Encyclopedia of Chemical Technology, 4th edition 1997). The hulls removed during such processing may be used as an integrated feedstream in the present method.

Cottonseed in the U.S. is processed into oil and meal by screw-pressing or solvent extraction. In screw-pressing the seed is cleaned, delinted, dehulled, flaked, and cooked prior to pressing. Screw-pressing yields a cake containing 2.5-4.0% residual oil. The cake is ground into a meal, and ground cottonseed hulls are blended back to adjust protein content to trading standards. In the solvent extraction procedure the flakes are often processed through an expander to rapidly cook the flakes and to form collets, which are then extracted with hexane. Meal emerging from the solvent extractors is freed of hexane by heating. (Kirk-Othmer Encyclopedia of Chemical Technology, 4th edition 1997). The hulls removed during such processing may be used as an integrated feedstream in the present method.

Grain process streams include a fiber stream composed of hulls that is produced during dry milling, fibrous milling residue from wet milling, spent grains streams produced in various processes, and the distiller dry grains and solubles (DDGS) and distiller dry grains (DDG) resulting from the dry grind processes. DDGS includes fiber, oil, protein and yeast and is the material remaining after removing ethanol from the fermentation mixture. The solids are filtered out to produce the DDG fraction, which is sold for animal feed. The remaining liquid fraction (stillage) may be recycled back as an in-process stream, or evaporated and combined with the DDG to form the DDGS co-product.

Another example of a potential source for alternative feedstreams includes root processing, such as processing of sugar beets, potatoes (white or sweet) etc. In sugar beet processing for sugar production, sugar is removed by a countercurrent extraction with water. The residual beet solids, or pulp, that exit the extraction apparatus are pressed to remove water and reduce the moisture level to approximately 75%. This pressed pulp can be sold as-is to local feed operations, but is more commonly mixed with molasses, dried to approximately 10% moisture and sold as cattle feed. (Kirk-Othmer Encyclopedia of Chemical Technology, 4th edition 1997). This pressed pulp, may be used as an integrated feedstream in the present method.

The alternative feedstreams used in the present method, in addition to fibrous process material, may also contain smaller amounts of components including protein, oil, and/or starch.

Applicants have found that combining processed seed materials, starch, and/or oil with biomass that is typically used in pretreatment, does not negatively impact the yield of fermentable sugars produced in the following saccharification treatment of the pretreated integrated feedstock using the present method. Further, expected sugar yield produced from the integrated feedstock in the present method may be based on the total cellulosic (including hemicellulosic) content of the integrated feedstock. Thus, the seed process streams may be added to other biomass for pretreatment, and the fiber in the process stream is pretreated along with the other biomass in preparation for saccharification to produce fermentable sugars. The effectiveness of using this integrated feedstock for pretreatment, provides an abundant, low-cost and continuously available feedstock for biomass processing facilities.

Pretreatment

The concentration of ammonia used in pretreatment of integrated feedstock in the present method is minimally a concentration that is sufficient to maintain the pH of the integrated feedstock-aqueous ammonia mixture alkaline and maximally less than about 12 weight percent relative to dry weight of integrated feedstock. This low concentration of ammonia is sufficient for pretreatment, and the low concentration may also be less than about 10 weight percent relative to dry weight of integrated feedstock. A very low concentration of 6 percent ammonia relative to dry weight of integrated feedstock, or less, also may be used for pretreatment. By alkaline is meant a pH of greater than 7.0. Particularly suitable is a pH of the integrated feedstock-aqueous ammonia mixture that is greater than 8. In one embodiment, ammonia is present at less than about 8 weight percent relative to dry weight of integrated feedstock. In one embodiment, ammonia is present at less than about 10 weight percent relative to dry weight of integrated feedstock. Particularly suitable is ammonia at less than about 6 weight percent relative to dry weight of integrated feedstock.

Ammonia as used in the present process provides advantages over other bases. Ammonia partitions into a liquid phase and vapor phase. Gaseous ammonia can diffuse more easily through biomass than a liquid base, resulting in more efficacious pretreatment at lower concentrations. Ammonia also competes with hydrolysis, via ammonolysis, of acetyl esters in biomass to form acetamide (as shown in CL2825, which is herein incorporated by reference, Example 11). Acetamide is less toxic than acetate to certain fermentation organisms, such as *Zymomonas mobilis* (as shown in CL2825, which is herein incorporated by reference, Example 12). Thus conversion of acetyl esters to acetamide rather than to acetic acid reduces the need to remove acetic acid. The use of ammonia also reduces the requirement to supplement growth medium used during fermentation with a nitrogen source. In addition, ammonia is a low-cost material and thus provides an economical process. Ammonia can also be recycled to the pretreatment reactor during pretreatment or following pretreatment, thus enabling a more economical process. For example, following pretreatment, as the temperature is decreased to that suitable for saccharification, ammonia gas may be released, optionally in the presence of a vacuum, and may be recycled. In a continuous process, ammonia may be continuously recycled.

According to the present method, the aqueous solution comprising ammonia may optionally comprise at least one additional base, such as sodium hydroxide, sodium carbonate, potassium hydroxide, potassium carbonate, calcium hydroxide and calcium carbonate. The at least one additional base may be added in an amount that is combined with ammonium to form an amount of total base that is less than about 20 weight percent relative to dry weight of biomass. Preferably the total second base plus ammonia is in an amount that is less than about 15 weight percent. Additional base(s) may be utilized, for example, to neutralize acids in biomass, to provide metal ions for the saccharification enzymes, or to provide metal ions for the fermentation growth medium.

In the present method, the dry weight of integrated feedstock is at an initial concentration of at least about 15% up to about 80% of the weight of the integrated feedstock-aqueous ammonia mixture. More suitably, the dry weight of integrated feedstock is at a concentration of from about 15% to about 60% of the weight of the integrated feedstock-aqueous ammonia mixture. The percent of integrated feedstock in the integrated feedstock-aqueous ammonia mixture is kept high to minimize the need for concentration of sugars resulting from saccharification of the pretreated integrated feedstock, for use in fermentation. The high integrated feedstock concentration also reduces the total volume of pretreatment material, making the process more economical.

The integrated feedstock may be used directly as obtained from the sources, or energy may be applied to the integrated feedstock to reduce the size, increase the exposed surface area, and/or increase the availability of cellulose, hemicellulose, and/or oligosaccharides present in the integrated feedstock to ammonia and to saccharification enzymes used in the second step of the method. Energy means useful for reducing the size, increasing the exposed surface area, and/or increasing the availability of cellulose, hemicellulose, and/or oligosaccharides present in the integrated feedstock to ammonia and to saccharification enzymes include, but are not limited to, milling, crushing, grinding, shredding, chopping, disc refining, ultrasound, and microwave. This application of energy may occur before or during pretreatment, before or during saccharification, or any combination thereof.

Pretreatment of integrated feedstock with ammonia solution is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and the steam gun reactor (Autoclave Engineers, Erie, Pa.). Much larger scale reactors with similar capabilities may be used. Alternatively, the integrated feedstock and ammonia solution may be combined in one vessel, then transferred to another reactor. Also integrated feedstock may be pretreated in one vessel, then further processed in another reactor such as the steam gun reactor (Autoclave Engineers, Erie, Pa.).

Prior to contacting the integrated feedstock with an aqueous solution comprising ammonia, vacuum may be applied to the vessel containing the integrated feedstock. By evacuating air from the pores of the integrated feedstock, better penetration of the ammonia into the integrated feedstock may be achieved. The time period for applying vacuum and the amount of negative pressure that is applied to the integrated feedstock will depend on the type of integrated feedstock and can be determined empirically so as to achieve optimal pretreatment of the integrated feedstock (as measured by the production of fermentable sugars following saccharification).

The contacting of the integrated feedstock with an aqueous solution comprising ammonia is carried out at a temperature of from about 4° C. to about 200° C. Initial contact of the integrated feedstock with ammonia at 4° C., allowing impregnation at this temperature, was found to increase the efficiency of saccharification. In another embodiment, said contacting of the integrated feedstock is carried out at a temperature of from about 75° C. to about 150° C. In still another embodiment, said contacting of the integrated feedstock is carried out at a temperature of from greater than 90° C. to about 150° C.

The contacting of the integrated feedstock with an aqueous solution comprising ammonia is carried out for a period of time up to about 8 hrs. Longer periods of pretreatment are possible, however a shorter period of time is preferable for practical, economic reasons.

In one embodiment, the pretreatment process may be performed at a relatively high temperature for a relatively short period of time, for example at from about 100° C. to about 150° C. for about 5 min to about 2 hr. In another embodiment, the pretreatment process may be performed at lower temperature for a relatively long period of time, for example from about 75° C. to about 100° C. for about 2 hr to about 8 hr. In still another embodiment, the pretreatment process may be performed at room temperature (approximately 22-26° C.) for an even longer period of time of about 24 hr. Other temperature and time combinations intermediate to these may also be used.

For the pretreatment process, the temperature, time for pretreatment, ammonia concentration, concentration of one or more additional bases, integrated feedstock concentration, integrated feedstock type and integrated feedstock particle size are related; thus these variables may be adjusted as necessary to obtain an optimal product to be contacted with a saccharification enzyme consortium.

A plasticizer, softening agent, or combination thereof, such as polyols (e.g., glycerol, ethylene glycol), esters of polyols (e.g., glycerol monoacetate), glycol ethers (e.g., diethylene glycol), acetamide, ethanol, and ethanolamines, may be added in the pretreatment process (i.e., step (a)). A plasticizer may be added as a component of the aqueous ammonia solution, as a separate solution, or as a dry component.

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-aqueous ammonia mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, N.Y.). The pretreatment reaction may be carried out as a batch process, or as a continuous process.

It is well known to those skilled in the art that a nitrogen source is required for growth of microorganisms during fermentation; thus the use of ammonia during pretreatment provides a nitrogen source and reduces or eliminates the need to supplement the growth medium used during fermentation with a nitrogen source. If the pH of the pretreatment product exceeds that at which saccharification enzymes are active, or exceeds the range suitable for microbial growth in fermentation, acids may be utilized to reduce pH. The amount of acid used to achieve the desired pH may result in the formation of salts at concentrations that are inhibitory to saccharification enzymes or to microbial growth. In order to reduce the amount of acid required to achieve the desired pH and to reduce the raw material cost of $NH_3$ in the present pretreatment process, ammonia gas may be evacuated from the pretreatment reactor and recycled.

In order to obtain sufficient quantities of sugars from integrated feedstock, the integrated feedstock may be pretreated with an aqueous ammonia solution one time or more than one time. Likewise, a saccharification reaction can be performed one or more times. Both pretreatment and saccharification processes may be repeated if desired to obtain higher yields of sugars. To assess performance of the pretreatment and saccharification processes, separately or together, the theoretical yield of sugars derivable from the starting integrated feedstock can be determined and compared to measured yields.

Following pretreatment, the product comprises a mixture of ammonia, partially degraded integrated feedstock and fermentable sugars. Prior to further processing, ammonia may be removed from the pretreated integrated feedstock by applying a vacuum. Removing ammonia lowers the pH, and thus less neutralizing acid is used to obtain the desired pH for saccharification and fermentation. This results in a lower salt load in the pretreatment mixture. Typically some ammonia remains, which is desired to provide a nitrogen source for fermentation.

In one preferred embodiment, the entire pretreatment mixture comprising both soluble and insoluble fractions is utilized in a saccharification reaction. In another embodiment, prior to saccharification, the aqueous fraction comprising ammonia and solubilized sugars may be separated from insoluble particulates remaining in the mixture. Methods for separating the soluble from the insoluble fractions include, but are not limited to, decantation and filtration. The insoluble particulates may be recycled to the pretreatment reactor. The insoluble particulates may optionally be washed with an aqueous solvent (e.g. water) to remove adsorbed sugars prior to being recycled to the pretreatment reactor. The insoluble fraction may then be subjected to additional treatment with aqueous ammonia solution as described above for pretreatment, followed by saccharification with a saccharification enzyme consortium. The soluble fraction may also be concentrated prior to saccharification using a suitable process, such as evaporation.

Second Integrated Feedstock—Combining after Pretreatment

In another aspect of the present method an alternative feedstream, such as a seed process stream, is combined with pretreated biomass to provide a second integrated feedstock that is saccharified. The pretreated biomass is material that has been pretreated as described herein, substituting biomass for integrated feedstock, or, an alternative feedstream, such as mentioned above, a seed process stream, is combined with pretreated integrated feedstock to provide a second integrated feedstock that is saccharified.

For the alternative feed stream that is a seed process stream, the seed process stream that may be combined with pretreated material includes material that is generally low in fiber, such as the stillage stream described herein above or corn steep liquor. Particularly useful is a seed process stream that provides a characteristic or component that is a benefit to saccharification, and/or to a fermentation sugar product. A benefit that may be provided by a seed process stream is in adjusting the pH of the pretreated material. A seed process stream that is acidic is of particular use where the pretreatment process is carried out at an alkaline pH. It is generally useful to reduce the pH prior to saccharification, to match the pH optimum of the sacharification enzyme consortium. For example, the stillage from dry grinding and ethanol fermentation described above, typically has a pH of between about 3 and 5. Addition of stillage to pretreated material will reduce the pH for the saccharification process.

In this method, where an alternative feedstream is integrated with pretreated biomass, (the biomass may or may not be a pretreated integrated biomass), the method of pretreatment is non-limiting. The pretreated biomass may have undergone other conventional methods of pretreatment, such as acid hydrolysis or other methods of pretreatment known in the art (see, e.g, U.S. Pat. No. 5,916,780).

In an aspect of this method the alternative feedstream is composed of stillage. Stillage typically contains amino acids and other nutrients from yeast fermentation that is beneficial in a fermentation sugar product. Thus, the fermentation sugar product resulting from saccharification of an integrated feedstock may contain fermentable sugars as well as other nutrients derived from a seed process stream. The presence of the nutrients may result in a reduced requirement for additional nutrients in the saccharification product prior to its use in biocatalyst fermentations.

Saccharification

In the present method, the following feedstocks may be saccharified: 1) a pretreated integrated feedstock; 2) a pretreated integrated feedstock that is combined post-pretreatment with at least one alternative feedstream to form a second integrated feedstock that is saccharified; or 3) a pretreated non-integrated biomass that is combined with at least one alternative feedstream post-pretreatment to form a second integrated feedstock. In the present method, one or more of the integrated feedstocks described above, numbering 1-3, is hydrolyzed in the presence of a saccharification enzyme consortium to release oligosaccharides and/or monosaccharides in a hydrolyzate. Saccharification in the present method is of an integrated feedstock, whether integration occurs prior to pretreatment, after pretreatment, or both. Saccharification enzymes and methods for biomass treatment are reviewed in Lynd, L. R., et al. (Microbiol. Mol. Biol. Rev. (2002) 66:506-577).

In one aspect of the present method, prior to saccharification, the aqueous fraction comprising ammonia and solubilized sugars may be separated from insoluble particulates remaining in the mixture. Methods for separating the soluble from the insoluble fractions include, but are not limited to, decantation and filtration. The insoluble particulates may be recycled to a pretreatment reactor. The insoluble particulates may optionally be washed with an aqueous solvent (e.g., water) to remove adsorbed sugars prior to being recycled to the pretreatment reactor. The insoluble fraction may then be subjected to additional treatment with aqueous ammonia solution as described above for pretreatment, followed by saccharification with a saccharification enzyme consortium. The soluble fraction may also be concentrated prior to saccharification using a suitable process, such as evaporation.

Prior to saccharification, the pretreatment product may be treated to alter the pH, composition or temperature such that the enzymes of the saccharification enzyme consortium will be active. The pH may be altered through the addition of an alternative feedstream, as described herein above, or of acids in solid or liquid form. Alternatively, carbon dioxide ($CO_2$), which may be recovered from fermentation, may be utilized to lower the pH. For example, $CO_2$ may be collected from a fermenter and fed, such as by bubbling, into the pretreatment product while monitoring the pH, until the desired pH is achieved. The temperature may be brought to a temperature that is compatible with saccharification enzyme activity, as noted below. Any cofactors required for activity of enzymes used in saccharification may be added.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995), Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the integrated feedstocks that they hydrolyze. Glycosidases useful for the present method include cellulose-hydrolyzing glycosidases (for example, cellulases, endoglucanases, exoglucanses, cellobiohydrolases, β-glucosidases), hemicelluose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the integrated feedstocks. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

As noted above, alternative feedstreams, such as high fiber and other seed process streams that may be used to form integrated feedstocks, may include a component of starch. This starch may be broken down into fermentable sugars using the starch-hydrolyzing glycosidases (for example, amylases, α-amylases, β-amylases, glucoamylases, β-glucosidases, isoamylases). Thus, when an alternative feedstream that includes starch is incorporated either prior to or after pretreatment, it is particularly suitable to include starch-hydrolyzing enzymes during saccharification in the present process to enhance fermentable sugar production.

The alternative feedstreams that may be used to form integrated feedstocks in the present methods may include a component of protein. Protein may be broken down using peptidases. Thus when a grain process stream that includes protein is incorporated either prior to or after pretreatment, it may be suitable to include protein-hydrolyzing enzymes during saccharification in the present process to enhance the fermentable sugar product with amino acids Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. The pH optimum can range from about 2 to about 11. In another embodiment, the pH optimum used with the saccharification enzyme consortium in the present method ranges from about 4 to about 10.

The saccharification can be performed for a time of about several minutes to about 120 hr, and preferably from about several minutes to about 48 hr. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, such as using hemicellulases followed by cellulases.

The degree of solubilization of sugars from the integrated feedstocks or the second integrated feedstocks following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentable sugars released from the integrated feedstocks or the second integrated feedstocks can be used by suitable microorganisms to produce target chemicals. Following saccharification, but prior to fermentation, the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the microorganism(s) used during fermentation and the pH used during saccharification, the pH may be adjusted to that suitable for fermentation. In addition, the saccharification mixture may be supplemented with additional nutrients required for microbial growth. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration. The saccharification mixture may be used as a component of a fermentation broth, for example, making up between about 90% and about 10% of the final medium.

Temperature and/or headspace gas may also be adjusted, depending on conditions useful for the fermentation microorganism(s). Fermentation may be aerobic or anaerobic. Fermentation may occur subsequent to saccharification, or may occur concurrently with saccharification by simultaneous saccharification and fermentation (SSF). SSF can keep the sugar levels produced by saccharification low, thereby reducing potential product inhibition of the saccharification enzymes, reducing sugar availability for contaminating microorganisms, and improving the conversion of pretreated biomass to monosaccharides and/or oligosaccharides.

Target chemicals that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include *Escherichia*, *Zymomonas*, *Saccharomyces*, *Candida*, *Pichia*, *Streptomyces*, *Bacillus*, *Lactobacillus*, and *Clostridium*. In another embodiment, biocatalysts may be selected from the group consisting of recombinant *Escherichia coli*, *Zymomonas mobilis*, *Bacillus stearothermophilus*, *Saccharomyces cerevisiae*, and *Pichia stipitis*.

Many biocatalysts used in fermentation to produce target chemicals have been described and others may be discovered, produced through mutation, or engineered through recombinant means. Any biocatalyst that uses fermentable sugars produced in the present method may be used to make the target chemical(s) that it is known to produce, by fermentation in the present method.

Fermentation of carbohydrates to acetone, butanol, and ethanol (ABE fermentation) by solventogenic *Clostridia* is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostndium beijerinckii* to produce high levels of butanol, also producing acetone and ethanol, is described in U.S. Pat. No. 6,358,717. Genetically modified strains of *E. coli* have also been used as biocatalysts for ethanol production (Underwood et al., (2002) Appl. Environ. Microbiol.68:6263-6272). A genetically modified strain of *Zymomonas mobilis* that has improved production of ethanol is described in US 2003/0162271 A1.

Lactic acid has been produced in fermentations by recombinant strains of *E. coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). Recombinant strains of *E. coli* have been used as biocatalysts in fermentation to produce 1,3 propanediol (U.S. Pat. Nos. 6,013,494, 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17cr1 (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-Ul-Haq et al., (2005)

Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid and 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium*, *Brevibacterium*, and *Serratia*. For example, production of histidine using a strain resistant to a histidine analog is described in Japanese Patent Publication No. 8596/81 and using a recombinant strain is described in EP 136359. Production of tryptophan using a strain resistant to a tryptophan analog is described in Japanese Patent Publication Nos. 4505/72 and 1937/76. Production of isoleucine using a strain resistant to an isoleucine analog is described in Japanese Patent Publication Nos. 38995/72, 6237/76, 32070/79. Production of phenylalanine using a strain resistant to a phenylalanine analog is described in Japanese Patent Publication No.10035/81. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 37235/79 and 150381/82) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. Nos. 6,861,237, 6,777,207, 6,228,630).

The pretreatment and saccharification of biomass to fermentable sugars, followed by fermentation of the sugars to a target chemical is exemplified in CL2825 (Example 9), which is herein incorporated by reference) for the production of ethanol from pretreated corn cobs using *Z. mobilis* as the biocatalyst for the fermentation of sugars to ethanol. The method of the present invention can also be used for the production of 1,3-propanediol from biomass. Biomass undergoes pretreatment and saccharification according to the present invention; following (or during) saccharification, *E. coli* is used to produce 1,3-propanediol as described in CL2825 (Example 10).

Target chemicals produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

EXAMPLES

General Methods and Materials

The following abbreviations are used:
"HPLC" is High Performance Liquid Chromatography, "C" is Centigrade, "kPa" is kilopascal, "m" is meter, "mm" is millimeter, "kW" is kilowatt, , "μm" is micrometer, "μL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass.

Sulfuric acid, ammonium hydroxide, acetic acid, acetamide, yeast extract, 2-morpholinoethanesulfonic acid (MES), potassium phosphate, glucose, xylose, tryptone, sodium chloride and citric acid were obtained from Sigma-Aldrich (St. Louis, Mo.).

Pretreatment and Enzymatic Hydrolysis Reactor (PEHR)

A biomass treatment apparatus with dimensions and features as shown in FIG. 2 and described herein above is called the PEHReactor and was used in the following Examples. Briefly, the 9L PEHReactor (constructed at NREL, Golden, CO; described in detail in co-pending application CL3447) has an approximately 15 cm×51 cm stainless steel reaction vessel with an injection lance for introduction of processing reactants. The injection lance is connected using a rotary joint to a port in a cover on one end of the vessel, which has an additional port for vessel access. Four baffles run the length of the vessel wall, and are attached perpendicularly to the wall. The baffles and twenty-two ceramic attrition media cylinders of 3.2 cm×3.2 cm (Advanced Ceramics, East Palestine, Ohio), free floating in the vessel, apply mechanical mixing of biomass and reactant as the vessel is rotated, promoting assimilation of reactant into the biomass. The PEHReactor is placed on a Bellco Cell-Production Roller Apparatus (Bellco Technology, Vineland, N.J.) which provides a mechanism for rotation, and the reactor with roller apparatus is housed in a temperature controlled chamber which provides heat. The temperature controlled chamber consists of an aluminum frame to support cork insulating pads surrounding the Bellco Cell Production Apparatus, to which a heater is attached that is controlled by thermocouples inserted through the center of the injection lance. Vacuum and pressure may be applied to the reaction vessel by attaching external sources to the lance-connected port in the cover.

Analytical Methods

Measurement of Sugar, Acetamide, Lactic Acid and Acetic Acid Content

Soluble sugars (glucose, cellobiose, xylose, galactose, arabinose and mannose) in saccharification liquor were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with appropriate guard columns. The sample pH was measured and adjusted to 5-6 with sulfuric acid if necessary. The sample was then passed through a 0.2 μm syringe filter directly into an HPLC vial. The HPLC run conditions were as follows:

HPX-87P (for carbohydrates):
Injection volume: 10-50 μL, dependent on concentration and detector limits
Mobile phase: HPLC grade water, 0.2 μm filtered and degassed
Flow rate: 0.6 mL/minute
Column temperature: 80-85° C., guard column temperature <60° C.
Detector temperature: as close to main column temperature as possible
Detector: refractive index
Run time: 35 minute data collection plus 15 minute post run (with possible adjustment for later eluting compounds)
Biorad Aminex HPX-87H (for carbohydrates)
Injection volume: 5-10 μL, dependent on concentration and detector limits
Mobile phase: 0.01 N Sulfuric acid, 0.2 μm filtered and degassed
Flow rate: 0.6 mL/minute
Column temperature: 55° C.
Detector temperature: as close to column temperature as possible
Detector: refractive index
Run time: 25-75 minute data collection After the run, concentrations in the sample were determined from standard curves for each of the compounds.

Example 1

Pretreatment and Saccharification of Combined Biomass Containing Corn Cobs and Different Spent Grain Samples in PEHReactor Spent grain samples were prepared from:
1. #2 yellow dent whole corn grain (purchased from Agway)
2. Corn grain degermed by the Quick Germ process developed at the University of Illinois (Singh and Eckoff (1996) Cereal Chem. 74: 462-466). Starting material was obtained from Vijay Singh at the University of Illinois.
3. Corn grain process by the Quick Fiber process to remove the germ and the hull fiber (U.S. Pat. No. 6,254,914). Starting material was obtained from Vijay Singh at the University of Illinois.
4. Brewers' grits were obtained from Cargill (Minneapolis, Minn.).

Spent grains refers to residual solids from grain processing in which starch is converted to sugar. Spent grains were produced essentially by a basic whiskey process. The different starting materials were treated with starch-degrading enzymes to produce sugars, and the resulting mash was filtered to retrieve the filter cake solids, or spent grains.

The starting materials were ground in a Foss (North American HQ: Eden Prarie, Minn.) Cyclotec 1093 sample mill (starting materials 1 and 2 above) to 250 μm or in a blender (starting materials 3 and 4 above), then combined with water and 200 mM $CaCl_2*H_2O$ in a 2L jacketed, stirred, glass reaction vessel. The pH of the mixture was adjusted to 6.5 with 1 N NaOH, and half of the total α-amylase (Spezyme HPA, Genencor International, Palo Alto, Calif.) was added. The reaction vessel was then heated to 95° C. and the remaining α-amylase was added 20 min later. After remaining at 95° C. for the specified time, the vessel was cooled to 70° C., and the pH of the mixture was adjusted to 4.5 with 1 M HCl. Glucoamylase (Gzyme 480, Genencor) was added, and the temperature was lowered further to 50° C. and held overnight. At this time, the reactor was cooled to <40° C., and the contents were filtered through Dacron filter cloth with a pore size of 10 μM. The filter cake was washed with water, and the final filter cake, or spent grains, was dried at 105° C. overnight and stored at room temperature until used in pretreatment experiments. Specific reaction conditions for each starting material are listed in the Table 1 below.

TABLE 1

Processing of spent grains samples.

| Starting material | Starting material added (g) | Water added (g) | α-amylase added (ml) | Total time at 95° C. | Glucoamylase added (ml) | Time at 50° C. (hr) |
|---|---|---|---|---|---|---|
| 1 | 375 | 1095 | 3 | 150 | 3 | 17 |
| 2 | 505 | 1095 | 3 | 150 | 3 | 23 |
| 3 | 1180 | 500 | 6 | 120 | 3 | 17.5 |
| 4 | 1160 | 500 | 6 | 120 | 3 | 18 |

Whole corn cobs were processed with a jaw crusher (2.2 kW motor) with a jaw spacing of approximately 0.95 cm, followed by a delumper (1.5 kW motor, Franklin Miller Inc.), followed by screening with a Sweco screen equipped with a 1.9 cm U.S. Standard screen. Fractured cobs were loaded with one type of spent grain, as listed in Table 3, into a PEHReactor. Spent grains were approximately 10% of the total dry weight of biomass in the reactor. Total dry biomass charge was approximately 473 g. Each charged reactor was preheated in the roller incubator to 95° C., without rotation, before the start of the experiment. A vacuum (approximately 85 kPa gauge pressure) was applied to the reaction vessel and the vessel was sealed off. When the temperature within each reaction vessel re-stabilized at 95° C., rotation was started at 19 rpm. Dilute ammonium hydroxide solution was added to give an ammonia concentration of 4 g ammonia/100 g dry weight of biomass and a solids concentration of 30 g dry weight of biomass/100 g total weight of biomass-ammonia mixture. Following injection, the vacuum on the vessel was relieved to atmospheric pressure. The reactor was maintained at 95° C. for 30 min, then the temperature was lowered to 85° C. where it was maintained for 4 hr with rotation. At the end of that time, a vacuum (approximately 85 kPa gauge pressure) was applied to the reactor vessel for 30 minutes to remove ammonia and drop the temperature of the contents of each reactor to approximately 50° C. Carbon dioxide was then injected into each reactor to relieve the vacuum and the reactors were pressurized to 138 kPa gauge pressure with $CO_2$ and rotated at pressure for 30 min at 50° C.

Following this, the reactor was depressurized, opened and the pH of the contents was adjusted to approximately 5.5 by injecting 75 ml of 1 M citric acid buffer, pH 4.8, into which citric acid monohydrate was added and dissolved. The citric acid buffer was injected into each reactor following heating to 50° C. and then allowed to equilibrate by incubating the reactors at 50° C. and 19 rpm for 1 hour. The reactors were removed from the incubator, opened, and the pH of a sample determined. If the pH was above 5.5, then additional solid citric acid monohydrate was added and the reactors were incubated with rotation at 50° C. for an additional hour. This process was repeated as often as necessary to obtain a pH for each reactor of ~5.5. Once the desired pH was reached, 28.4 mg/g cellulose Spezyme® CP cellulase (Genencor) and 10.1 mg active protein/g cellulose of Diversa D2 cocktail containing a beta-glucosidase, xylanase, beta-xylosidase and arabinfuranosidase were loaded into the reactor. The reactors remained in the incubator at 50° C. and 19 rpm for 72 hr. Following this pretreatment and saccharification, sugar yields were assayed as described in General Methods. Glucose and xylose yields, based on total glucan and xylan coming in with both feeds, are shown in Table 2. Yields of the cob plus spent grain combination biomass samples were similar to yields of the cob alone sample.

TABLE 2

Sugar yields following pretreatment and saccharification of combined biomass feeds.

| | Monomer glucose | Total glucose yield | Monomer xylose yield | Total xylose yield |
|---|---|---|---|---|
| Cob only (avg of 2) | 68.2% | 85.6% | 41.8% | 88.9% |
| Cob + Quick Germ spent grains | 67.9% | 86.5% | 49.0% | 86.5% |
| Cob + Quick Fiber spent grains | 69.5% | 88.3% | 54.6% | 87.3% |
| Cob + Brewers Grits spent grains | 65.6% | 79.5% | 48.3% | 83.2% |

Example 2

Pretreatment and Saccharification of Combined Biomass Containing Corn Cobs, Spent Grain, and Additional Components in the PEHReactor Fractured cobs and whiskey spent grains, prepared as described in Example 1, were combined in the PEHReactor as described in Example 1. In addition, other grain components were added. In one sample, starch (Sigma S4126, lot #093K0033) was added at 5 g/100 g total dry weight of biomass. In another sample, corn oil (Sysco Classic corn oil, lot #4119095) was added at a level of about 2 g/100 g total dry biomass. The samples were pretreated and saccharified as described in Example 1. Results are shown in Table 3. These results also compare favorably with the cob only control data in Table 2.

TABLE 3

Sugar yields resulting from pretreatment and saccharification of cob, spent grains and additional grain components.

| | Monomer glucose | Total glucose yield | Monomer xylose yield | Total xylose yield |
|---|---|---|---|---|
| Cob + whiskey spent grains + starch | 70.4% | 90.2% | 48.4% | 96.1% |
| Cob + whiskey spent grains + oil | 79.2% | 87.5% | 54.9% | 101.4% |

Example 3

Pretreatment and Saccharification of Combined Biomass Containing Corn Cobs and Corn Fiber in the PEHReactor Fractured corn cobs and Cargill Bran 80 (Cargill, Minnetonka, Minn.) corn fiber were combined such that the fiber was approximately 10% of the total dry biomass. The combined biomass was pretreated and saccharified as described in Example 1. The resulting sugar yields are shown in Table 4. Yields of the cob plus corn fiber combination biomass were similar to yields of the cob alone sample.

TABLE 4

Sugar yields resulting from pretreatment of corn cobs combined with corn fiber.

| | Monomer glucose | Total glucose yield | Monomer xylose yield | Total xylose yield |
|---|---|---|---|---|
| Cob + Cargill Bran 80 | 66.4% | 82.3% | 47.0% | 83.5% |

What is claimed is:

1. A method of treating biomass composed of integrated feedstocks, said method comprising:
   a) providing biomass;
   b) adding to the biomass of a) at least one alternative feedstream to produce an integrated feedstock;
   c) for a period of time up to about 25 hours, contacting the integrated feedstock of b) with an aqueous solution comprising ammonia to form an integrated feedstock-aqueous ammonia mixture, wherein the ammonia is present at a concentration at least sufficient to maintain alkaline pH of the integrated feedstock-aqueous ammonia mixture, wherein said ammonia is present at 12 weight percent or less relative to dry weight of integrated feedstock, and further wherein the dry weight of integrated feedstock is at a solids concentration of about 15 weight percent or more relative to the weight of the integrated feedstock-aqueous ammonia mixture, to produce a pretreated integrated feedstock product; and
   d) contacting the product of c) with a saccharification enzyme consortium comprising one or more hemicellulose-hydrolyzing glycosidase, under suitable conditions to produce a fermentable sugar product, wherein said fermentable sugar product provides a carbohydrate source for a biocatalyst for a fermentation process.

2. The method of claim 1 wherein the pH of the integrated feedstock-aqueous ammonia mixture is greater than 8.

3. The method of claim 1 wherein said dry weight of integrated feedstock is at an initial concentration of from about 15% to about 80% relative to the weight of the integrated feedstock-ammonia mixture.

4. The method of claim 3 wherein said dry weight of integrated feedstock is at an initial concentration of from about 15% to about 60% relative to the weight of the integrated feedstock-ammonia mixture.

5. The method of claim 1 wherein said ammonia is present at 10 or less weight percent relative to dry weight of integrated feedstock.

6. The method of claim 1 wherein said ammonia is present at 6 or less weight percent relative to dry weight of integrated feedstock.

7. The method of claim 1 wherein step (c) is carried out a temperature of from about 4° C. to about 200° C.

8. The method of claim 7 wherein the step (c) is carried out a temperature of from about 75° C. to about 150° C.

9. The method of claim 8 wherein the step (c) is carried out a temperature of from greater than 90° C. to about 150° C.

10. The method of claim 1 wherein step (c) is carried out for a period of time of up to about 8 hours.

11. A method of treating biomass composed of integrated feedstocks, said method comprising:
   a) providing biomass;
   b) subjecting the biomass of a) to a pretreatment process to produce a pretreated biomass product, wherein said pretreatment process comprises the step of for a period of time up to about 25hours, contacting the biomass of a) with an aqueous solution comprising ammonia to form a biomass-aqueous ammonia mixture, wherein the ammonia is present at a concentration at least sufficient to maintain alkaline pH of the biomass-aqueous ammonia mixture, wherein said ammonia is present at 12weight percent or less relative to dry weight of biomass, and further wherein the dry weight of biomass is at a solids concentration of about 15 weight percent or more relative to the weight of the biomass-aqueous ammonia mixture;
   c) adding to the pretreated biomass product of b) at least one alternative feedstream to produce a first and optionally a second integrated feedstock; and
   d) contacting the first or, if present, the second integrated feedstock of c) with a saccharification enzyme consortium comprising one or more hemicellulose-hydrolyzing glycosidase, under suitable conditions, to produce a fermentable sugar product wherein said fermentable sugar product provides a carbohydrate source for a biocatalyst for a fermentation process.

12. The method of claim 11 wherein the pH of the biomass-aqueous ammonia mixture is greater than 8.

13. The method of claim 11 wherein said dry weight of biomass is at an initial concentration of from about 15% to about 80%.

14. The method of claim 11 wherein said dry weight of biomass is at an initial concentration of from about 15% to about 60%.

15. The method of claim 11 wherein said ammonia is present at 10 or less weight percent relative to dry weight of biomass.

16. The method of claim 15 wherein said ammonia is present at 6 or less weight percent relative to dry weight of biomass.

17. The method of claim 11 wherein step (b) is carried out a temperature of from about 4° C. to about 200° C.

18. The method of claim 17 wherein the step (b) is carried out at a temperature of from about 75° C. to about 150° C.

19. The method of claim 18 wherein the step (b) is carried out a temperature of from greater than 90° C. to about 150° C.

20. The method of claim 11 wherein step (b) is carried out for a period of time of up to about 8 hours.

21. The method of claim 11 wherein the biomass of step a) is an integrated feedstock.

22. The method of claim 11 wherein the alternative feedstream is composed of stillage.

23. The method of claim 1 or 11 wherein biomass is selected from the group consisting of bioenergy crops, agricultural residues, municipal solid waste, industrial solid waste, yard waste, wood and forestry waste.

24. The method of claim 1 or 11 wherein biomass is selected from the group consisting of switchgrass, waste paper, sludge from paper manufacture, corn grain, corn cobs, corn husks, corn stover, grasses, wheat, wheat straw, hay, rice straw, sugar cane bagasse, sorghum, soy, trees, branches, roots, leaves, wood chips, sawdust, shrubs and bushes, vegetables, fruits, flowers and animal manure.

25. The method of claim 1 or 11 wherein biomass is selected from the group consisting of corn cobs, corn stover, corn husks, sugar can bagasse, switchgrass, wheat straw, hay, barley, barley straw, rice straw, and grasses.

26. The method of claim 25 wherein biomass is selected from the group consisting of corn cobs, corn stover and sugar cane bagasse.

27. The method of claim 1 or 11 wherein ammonia is selected from the group consisting of ammonia gas, ammonium hydroxide, urea, and combinations thereof.

28. The method of claim 1 or 11 wherein said aqueous solution comprising ammonia further comprises at least one additional base.

29. The method of claim 1 or 11 wherein ammonia is recycled.

30. The method of claim 1 or 11 wherein the alternative feedstream is selected from the group consisting of a co-product, an in-process stream, and a waste stream.

31. The method of claim 30 wherein alternative feedstream is a seed process stream from corn, oats, wheat, barley, rice, canola, sunflower, cotton, pea, or soybean, and other legumes.

32. The method of claim 1 or 11 wherein said saccharification enzyme consortium further comprises at least one additional enzyme selected from the group consisting of cellulose-hydrolyzing glycosidases, starch-hydrolyzing glycosidases, peptidases, lipases, ligninases and feruloyl esterases.

33. The method of claim 1 or 11 wherein said saccharification enzyme consortium comprises at least two enzymes selected from the group consisting of cellulases, endoglucanases, exoglucanases, cellobiohydrolasese, β-glucosidases, xylanases, endoxylanases, exoxylanases, β-xylosidases, arabinoxylanases, mannases, galactases, pectinases, glucuronidases, amylases, α-amylases, β-amylases, glucoamylases, α-glucosidases, and isoamylases.

34. The method of claim 1 or 11 wherein step (d) is performed at a temperature of from about 15° C. to about 100° C. and at a pH of from about 2 to about 11.

35. The method of claim 11, wherein the biomass of a) is composed of at least one alternative feedstream.

36. The method of claim 23, wherein said stillage is employed to reduce the pH of the pretreated material.

37. The method of claim 1 or 11, wherein said fermentable sugar product is used to produce value-added chemicals, plastics, or fuels.

* * * * *